(12) United States Patent
Masumura

(10) Patent No.: US 7,898,649 B2
(45) Date of Patent: Mar. 1, 2011

(54) MEASUREMENT METHOD AND MEASUREMENT APPARATUS

(75) Inventor: Takahiro Masumura, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 335 days.

(21) Appl. No.: 12/207,924

(22) Filed: Sep. 10, 2008

(65) Prior Publication Data

US 2009/0066949 A1 Mar. 12, 2009

(30) Foreign Application Priority Data

Sep. 12, 2007 (JP) ............................. 2007-237010

(51) Int. Cl.
*G01N 21/00* (2006.01)
(52) U.S. Cl. ..................... 356/73; 356/72; 356/402; 600/310; 600/473
(58) Field of Classification Search .............. 356/72, 356/73; 600/310, 473
See application file for complete search history.

(56) References Cited

U.S. PATENT DOCUMENTS

| 5,840,023 | A | 11/1998 | Oraevsky et al. ............ 600/407 |
| 6,738,653 | B1 | 5/2004 | Sfez et al. .................... 600/322 |
| 6,957,096 | B2 | 10/2005 | Sfez et al. .................... 600/407 |
| 2008/0058638 | A1* | 3/2008 | Zhu et al. .................... 600/425 |
| 2009/0002685 | A1* | 1/2009 | Fukutani et al. ............... 356/72 |

FOREIGN PATENT DOCUMENTS

| JP | 2005-331292 | 12/2005 |
| WO | 2007/100937 | 9/2007 |

OTHER PUBLICATIONS

L. V. Wang., "Mechanisms of Ultrasonic Modulation of Multipy Scattered Coherent Light: An Analytic Model", *Physical Review Letters*, vol. 87, No. 4, Jul. 23, 2001 (pages numbered 043903-1 through 043903-4).
G. Yao et al., "Signal Dependence and Noise Source in Ultrasound-Modulated Optical Tomography", *Applied Optics*, vol. 43, No. 6, Feb. 20, 2004, pp. 1320-1326.
U.S. Appl. No. 12/203,279, filed Sep. 3, 2008, Masumura et al.
U.S. Appl. No. 12/209,092, filed Sep. 11, 2008, Nishihara et al.
U.S. Appl. No. 12/209,258, filed Sep. 12, 2008, Yoshida et al.
DA Boas et al., "Imaging the Body with Diffuse Optical Tomography", *IEEE Signal Processing Magazine*, Nov. 2001, pp. 57-75.
CA DiMarzio et al., "Medical Imaging Techniques Combining Light and Ultrasound", *Subsurface Sensing Technologies and Applications*, vol. 4, No. 4 (Oct. 2003), pp. 289-309.

* cited by examiner

*Primary Examiner*—F. L Evans
(74) *Attorney, Agent, or Firm*—Fitzpatrick, Cella, Harper & Scinto

(57) ABSTRACT

A measurement method of measuring a spectroscopic characteristic inside of a scattering medium includes a first step of measuring the spectroscopic characteristic of the scattering medium by using diffuse optical tomography by irradiating light into the scattering medium, a second step of measuring the spectroscopic characteristic of the scattering medium by using acousto-optical tomography or photo acoustic tomography by irradiating light into the scattering medium, and a third step of making an assumption of a distribution of the spectroscopic characteristic inside of the scattering medium and of changing the assumption such that a difference between a predicted value of the spectroscopic characteristic derived from the assumption and a measured value obtained in the first step can fall upon a permissible range. The third step uses data obtained in the second step for at least one of the parameter: an initial value, a constraint condition, or a boundary condition.

6 Claims, 9 Drawing Sheets

MEASUREMENT METHOD AND MEASUREMENT APPARATUS

BACKGROUND OF THE INVENTION

1. Field of the Invention

The present invention relates to a measurement method and measurement apparatus configured to measure a spectroscopic characteristic inside a scattering medium (specimen).

2. Description of the Related Art

A conventional measurement apparatus as used for the optical mammography can create an image of a spatial distribution of a spectroscopic characteristic or metabolism of a biological tissue by measuring a spectroscopic characteristic or an attenuation characteristic in the biological tissue. The spectroscopic characteristic includes an absorption (spectroscopic) characteristic and a scattering (spectroscopic) characteristic, which will be also referred as an absorption-scattering characteristic in this application. Diffuse optical tomography ("DOT") is known as a conventional measurement method.

DOT introduces the near infrared light into a scattering medium, and detects the diffused light, as disclosed in Japanese Patent Laid-Open No. ("JP") 2005-331292. JP 2005-331292 assumes an internal distribution of a spectroscopic characteristic, and uses an algorithm that changes the assumption or reconstructs the assumed internal distribution based on a measurement result.

Other prior art include U.S. Pat. Nos. 6,738,653, 5,840,023, 6,957,096, and Lihong V. Wang, "Mechanism of Ultrasonic Modulation of Multiply Scattered Coherent Light: An Analytical Model," Phys. Rev. Lett., vol. 87, No. 4, 2001 and Gang Yao and Lihong Wang, "Signal dependence and noise source in ultrasound-modulated optical tomography," Appl. Opt. vol. 43, No. 6, 2004.

The image reconstruction method described in JP 2005-331292 requires complex, huge, and time-consuming calculations for the internal distribution, and is less likely to converge to an optimal solution quickly. A finer resolution is required for DOT measurement result.

SUMMARY OF THE INVENTION

The present invention is directed to a measurement method and measurement apparatus configured to relatively easily measure a distribution of a spectroscopic characteristic of a scattering medium with a fine resolution.

A measurement method according to one aspect of the present inventions is configured to measure a spectroscopic characteristic inside of a scattering medium. The measurement method includes a first step of measuring the spectroscopic characteristic of the scattering medium by using diffuse optical tomography by irradiating light into the scattering medium, a second step of measuring the spectroscopic characteristic of the scattering medium by using acousto-optical tomography or photo acoustic tomography by irradiating light into the scattering medium, and a third step of making an assumption of a distribution of the spectroscopic characteristic inside of the scattering medium and of changing the assumption such that a difference between a predicted value of the spectroscopic characteristic derived from the assumption and a measured value obtained in the first step can fall upon a permissible range. The third step uses data obtained in the second step for at least one of the parameter: an initial value, a constraint condition, or a boundary condition.

Further detailed objects and other characteristics of the present invention will become apparent by the preferred embodiments described below referring to accompanying drawings which follow.

DESCRIPTION OF THE EMBODIMENTS

Referring now to the accompanying drawings, descriptions will be given according to embodiments of the present invention.

First Embodiment

Figure 1A:
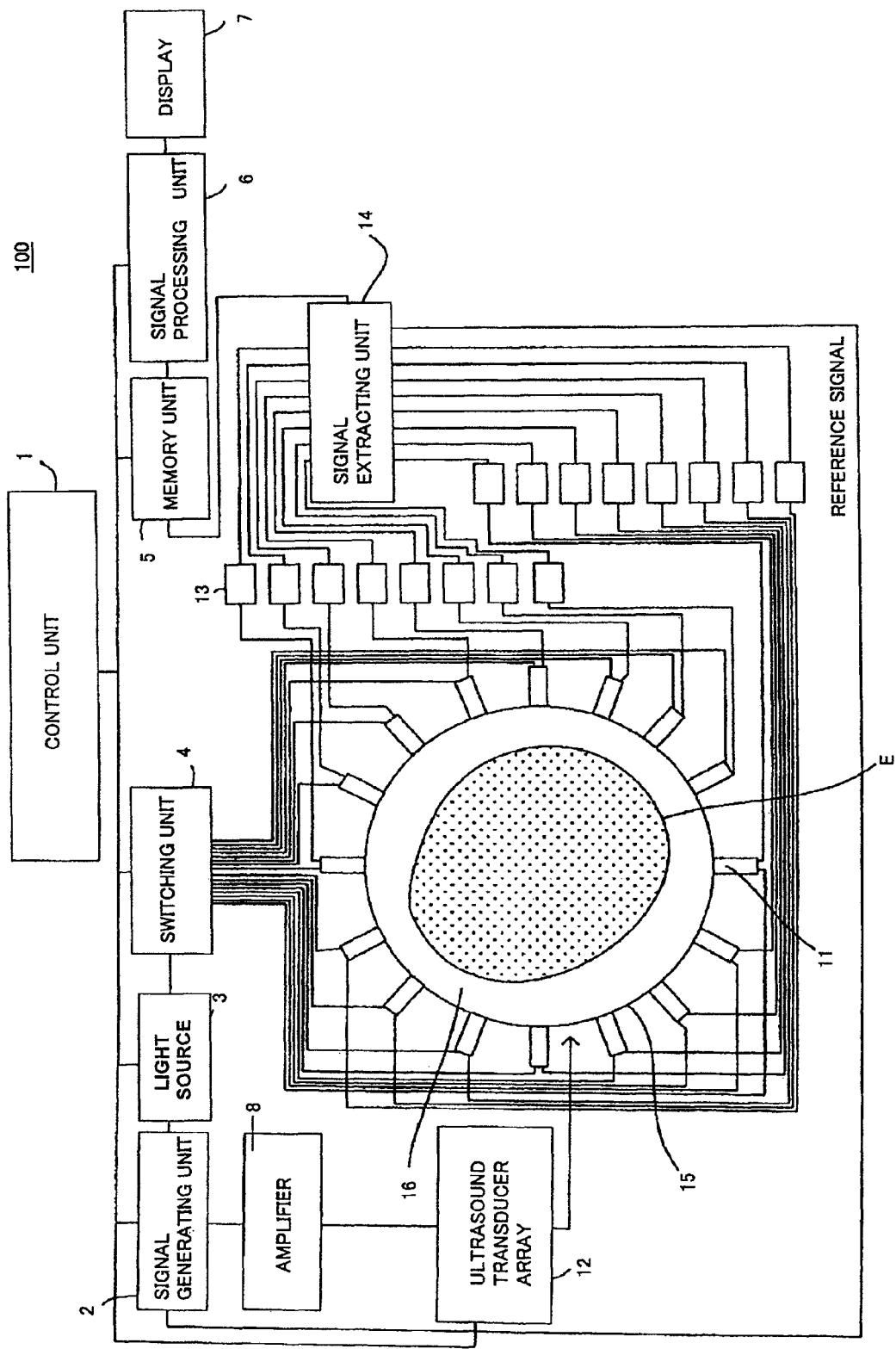
FIG. 1A is a block diagram of a measurement apparatus according to a first embodiment of the present invention and FIG. 1B is a schematic sectional view of the measurement apparatus shown in FIG. 1A.

FIG. 1A is a block diagram of a measurement apparatus 100 according to a first embodiment. The measurement apparatus 100 is configured to measure an absorption-scattering characteristic that is a spectroscopic characteristic in the tissue E using AOT or PAT, and to use the data to estimate a distribution of the spectroscopic characteristic, thereby quickly and reliably obtaining an optimal solution. The measurement apparatus 100 includes a first measurement unit and a second measurement unit.

AOT stands for acousto-optical tomography, and PAT stands for photo-acoustic tomography. AOT irradiates the coherent light and focused ultrasound into the biological tissue, and detects through a light detector (a light detecting unit) the modulated light as a result of a light modulation effect (or an acousto-optical effect) in an ultrasound focusing area (a measurement site), as disclosed in U.S. Pat. No. 6,738,653. PAT utilizes a difference in absorption factor of the light energy between a measurement site, such as a tumor, and another tissue, and receives through a transducer an elastic wave (ultrasound or a photoacoustic signal) that occurs as a result of that the measurement site absorbs the irradiated light energy and instantly swells. PAT is disclosed, for example, in U.S. Pat. No. 5,840,023.

Figure 1B:
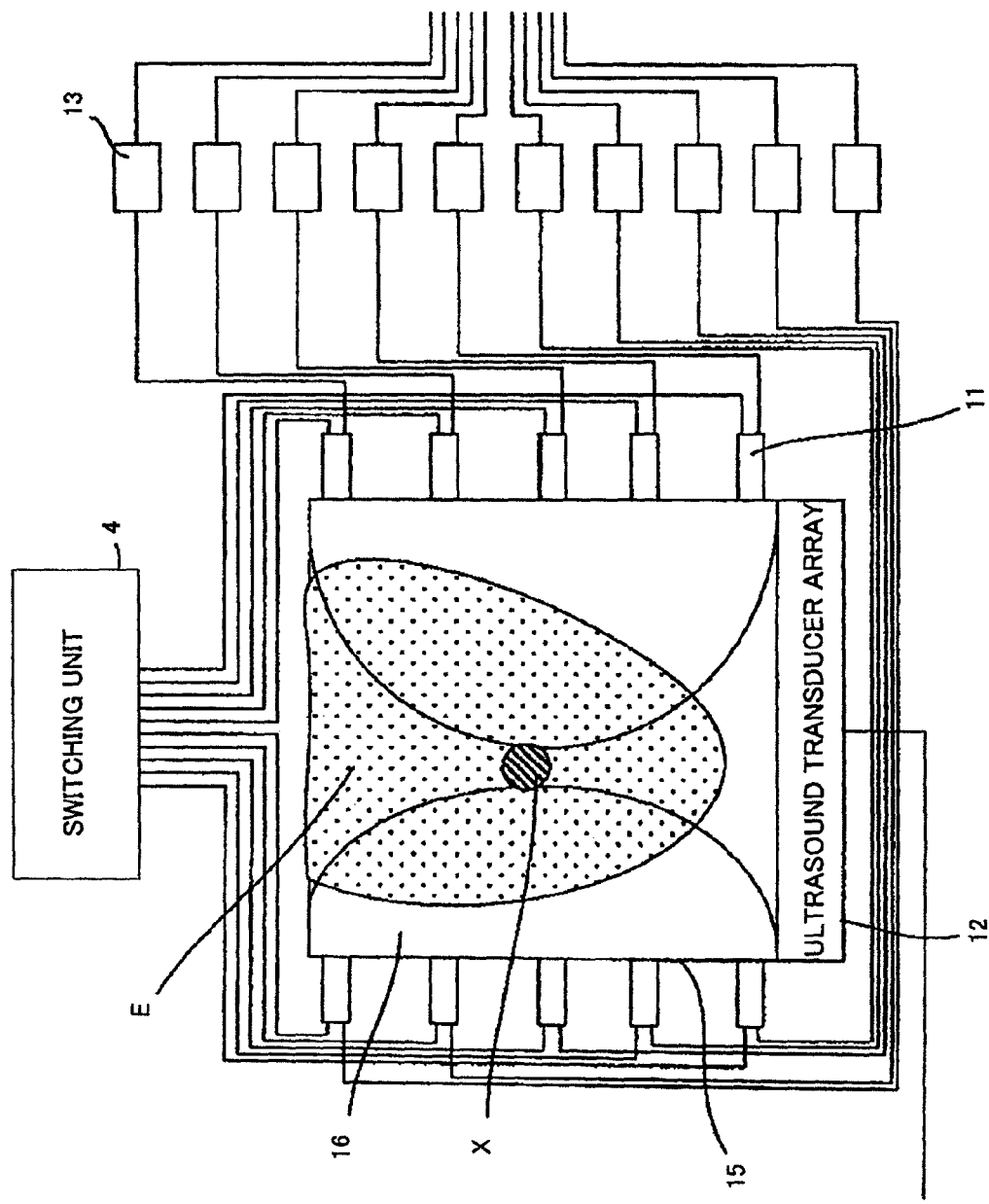

The scattering medium (specimen) E is a biological tissue, such as a human breast The scattering medium E is housed in a measurement vessel 15 shown in FIG. 1B. FIG. 1B is a schematic perspective view of the measurement vessel 15. A medium (or matching material 16) having a known and uniform characteristic is filled in a space between the scattering medium E and the measurement vessel 15. The medium has substantially the same refractive index of the light, scattering coefficient, and acoustic characteristic of the ultrasound as those of the scattering medium E.

The first measurement unit measures a spectroscopic characteristic of the scattering medium E by using DOT. The signal generating unit 2 generates a sine wave signal of a frequency f. The sine wave signal generated by the signal generating unit 2 is used to drive a light source 3. In general, a sine wave having several tens to hundreds of MHz modulates the light intensity in a bioinstrumentation. The light source 3 provides plural luminous fluxes having plural wavelengths. The light source 3 uses a light source that can supply the coherent light, such as a laser. A wavelength of the light source is selected among plural wavelengths in accordance with absorption spectra of water, lipid, protein, oxygenated hemoglobin, and deoxygenated hemoglobin. In an example, an appropriate wavelength falls upon a range between 600 and 1500 nm, because that light can highly transmit due to a small absorption of water that is a main ingredient in the biological tissue, and provides a characteristic spectrum for lipid, oxygenated hemoglobin, and deoxygenated hemoglobin. Due to a signal from the signal generating device 2, the light source 3 emits intensity modulated light having a frequency f, which will be, in turn, transmitted to a fiber 11. The fiber 11 is connected to a side surface of the measurement vessel 15, and a switching unit 4 is placed between the measurement vessel 15 and the light source 3.

The switching unit 4 has a switching mechanism such as a shutter, which allows the light emitted from the light source 3 to enter one of n fibers 11 as designated by a control unit 1 and blocks the light from entering the remaining n-1 out of n fibers 11. The n-1 fibers 11 introduces to a light detector 13 diffused light that has been emitted from the side surface of the measurement vessel 15, and passed the scattering medium E or the matching material 16. The switching unit 4 blocks an optical path to the light detector 13 from the fiber 11 that introduces the light from the light source to the measurement vessel 15. One fiber 11 that introduces the light from the light source 3 to the measurement vessel is exclusive to and n-1 fibers 11 which introduces the diffused light from the measurement vessel 15 to the light detector 13.

The light incident upon the measurement vessel 15 from the fiber 11 repeats absorptions and scatterings in the matching material 16 and the scattering medium E several times, and then propagates as diffused light in various directions. The light propagation in the scattering medium, such as the medium E and the matching material 16, can be described by a light diffusion equation. A fluence rate of a photon is given by the following equation where r is a position in the scattering medium, and t is time.

$$\frac{\partial \Phi(r,t)}{\partial t} = D\nabla^2 \Phi(r,t) - v\mu_a \Phi(r,t) + vS(r,t) \quad \text{EQUATION 1}$$

$\phi(r, t)$ is a fluence rate of a photon [number of photons/(mm$^2$·sec)]. D (=v/3$\mu_s'$) is a diffusion coefficient [mm$^2$/sec]. $\mu_s'$ is a reduced scattering coefficient [1/mm]. v is the light speed in the scattering medium [mm/sec]. $\mu_a$ is an absorption coefficient [1/mm]. S (r, t) is a radiation photon flux density of the light source [number of photons/(mm$^3$·sec)].

The intensity modulated light incident upon the measurement vessel 15 from the fiber 11 in the scattering medium propagates as an energy-density wave in the medium, which is referred as a diffused photon density wave of frequency f as derived from Equation 1. For example, if the light from the light source propagates by a distance r in an infinite and uniform medium, the light intensity $I_{AC}$ (r, $\omega$) and the phase $\Theta$ (r, $\omega$) of the density wave are given by the following equations:

$$I_{AC}(r,\omega) = \frac{vS_0}{4\pi Dr} \exp\left[\frac{-r\left(\frac{v\mu_a}{2D}\right)^{1/2}}{\left\{\left(1+\frac{\omega^2}{v^2\mu_a^2}\right)^{1/2}+1\right\}^{1/2}}\right] \quad \text{EQUATION 2}$$

$$\Theta(r,\omega) = r\left(\frac{v\mu_a}{2D}\right)^{1/2}\left\{\left(1+\frac{\omega^2}{v^2+\mu_a^2}\right)^{1/2}-1\right\}^{1/2} + \phi_0 \quad \text{EQUATION 3}$$

$\omega$(=2$\pi$f) is an angular frequency [rad/sec]. $S_0$ is a number of incident photon [number of photons/sec] $\phi_0$ is a phase of the light source [rad/sec]. The light detector 13 detects the light intensity of the diffused photon density wave via the n-1 fibers 11.

A signal detected by the light detector 13 is transmitted to a signal extracting unit 14. The signal extracting unit 14 uses as a reference signal a signal transmitted from the signal generating unit 2, and calculates an amplitude and phase of the diffused photon density wave described in Equations 2 and 3 based on the signal detected by the light detector 13. This is performed for all signals from n-1 fibers. As shown in Equations 2 and 3, the amplitude and the phase of the diffused photon density wave depend upon the absorption coefficient and the scattering coefficient in the media. However, Equations 2 and 3 are ideal analytical solutions, and practically as described later, use a result of Equation 1 solved according to a boundary condition of a measurement system or a result of Equation 1 solved with a numerical calculation using a finite element method etc.

Data on the amplitude and the phase calculated by the signal extracting unit 14 are sent to and saved in a memory unit 5. The measurement condition that specifies the fiber used as a light source is saved in the memory unit 5 along with the measurement data. The measurement is repeated n times such that each of n fibers can become a light source, and all of the measurement data are saved in the memory unit 5 (first step).

The fiber 11 may be three-dimensionally arranged on the side surface of the measurement vessel 15, or obtain three-dimensional data by vertically scanning, along the side surface of the measurement vessel 15, a module having the fibers 11 that are two-dimensionally arranged on one section.

Data obtained by the first measurement unit will be referred as first measurement data. The first measurement unit uses an intensity modulated light for the light source 3 and solves Equation 1 in a frequency domain, but may use picosecond pulsed light for the light source 3 and solve Equation 1 in a time domain.

The second measurement unit measures the spectroscopic characteristics in a second range in the scattering medium E by using AOT or PAT (although this embodiment uses AOT).

The control unit 1 controls the signal measurement device 2 to emit the continuous light from the light source 3. Similarly, the light emitted from the light source 3 is guided to the fiber 11. The control unit 1 controls the switching unit 4 to select one of the fibers 11 as a light source. Via the selected fiber 11, the light from the light source 3 enters the side surface of the measurement vessel 15. The light which enters the measurement vessel 15 propagates inside the measurement vessel 15 while similarly repeating absorptions and scatterings.

A signal from the signal generating device 2 is also used to continuously drive the ultrasonic transducer array 12 via the amplifier 8 under control of the control unit 1. The ultrasonic transducer array 12 operates an individual ultrasonic transducer such that the ultrasound is focused in the measurement site (the ultrasound focusing area) X in the measurement vessel 15, which is designated by the control unit 1, and emits ultrasound of a frequency $\Omega$. The ultrasound emitted from the ultrasonic transducer array 12 is focused with a spot of approximately several mm at the focusing position. In this way, the ultrasonic transducer array 12 serves both as an ultrasound generating device and an ultrasound focusing unit.

The medium density changes in the ultrasound focusing area, and causes a change in a refractive index of the medium and a displacement of the scatters depends upon the frequency of the irradiated ultrasound. The optical phase changes in response to ultrasonic modulation of the index of refraction and ultrasound-induced displacements of scatters, and the wavelength changes due to the Doppler shift when the light passes through the measurement site X. This phenomenon will be referred to as an acousto-optical effect. A light modulation effect in the ultrasound focusing area is analytically modeled in "Mechanism of Ultrasonic Modulation of Multiply Scattered Coherent Light: An Analytical Model," and an effect by the absorption coefficient is described in "Signal dependence and noise source in ultrasound-modulated optical tomography."

Use of the model can provide light intensity $\Psi(r_i)$ at one position $r_i$ detected as a result of the modulation depth by the ultrasound that passes through the ultrasound focusing area in the scattering medium, as described in U.S. Pat. No. 6,957,096, for example, as follows:

$$\Psi(r_i) = S_0 \Phi(r_s, r_i) m(\mu_a, \mu_s') \Phi(r_i, r_d) \qquad \text{EQUATION 4}$$

$\Phi(r_s, r_i)$ is a fluence rate of a photon from the position $r_s$ to the position $r_i$ of the light source. $\Phi(r_s, r_d)$ is a fluence rate of the photon from the position $r_s$ to a position $r_d$ of the light detector. $m(\mu_a, \mu_s')$ is a modulation depth by the ultrasound.

The light detector 13 simultaneously detects the modulated light that has passed through the measurement site X, and been modulated by the ultrasound, and the non-modulated light that has not modulated by the ultrasonic. The signal extracting unit 14 measures a modulated signal that is expressed by Equation 4 and modulated with the frequency $\Omega$ of the ultrasonic. The signal can be extracted by using a band pass filter or a lock-in detector in order to detect the signal efficiently.

Data obtained by the second measurement unit will be referred to as second measurement data. The second measurement data is stored in the memory unit 5 separately from the first measurement data. As well as the first measurement, the second measurement data is stored in the memory unit 5 for each parameter necessary for an image reconstruction such as a fiber used as a light source, an ultrasound focusing position, and an ultrasound irradiation intensity.

The fiber 11 selected as a light source may be closer to the measurement site X in order to improve the intensity of the modulated light by the ultrasound. In addition, in order to improve the resolution, the ultrasound transducer array 12 may be driven by a signal having a pulse width of between sub-micro seconds and several microseconds instead of a continuous signal generated by the signal generating unit 2. A plurality of ultrasound focusing positions are set at arbitrary positions inside the measurement vessel 15, and the data obtained by the second measurement unit is transmitted to the memory unit 5 (second step).

The second measurement unit may use another optical path of the reference light and provide a heterodyne detection. Then, an array sensor such as "CCD" or "CMOS" may be used for a speckle parallel measurement at the light detector 13. Alternatively, a measurement method that arranges a photorefractive element at a merging section between the reference light and the signal light, and uses a light detector, such as a PMT, may be used to improve the SN ratio of the signal.

Once the measurement of the first measurement unit and the measurement of the second measurement unit end, the signal processing unit 6 reads out first and second measurement data from the memory unit 5, and reconstructs an image. The signal processing unit 6 sequentially reads out and processes the data required for the image reconstruction from the memory unit 5. For example, the image reconstruction may use a method that estimates a light diffusion equation by using a finite element method. The medium in the measurement vessel 15 is cut into meshes so as to provide an absorption coefficient $\mu_a^{ij}$ and a scattering coefficient $\mu_s^{ij}$ at a position coordinate (i, j) of each mesh. For a distribution $P_{ij}(\mu_a^{ij}, \mu_s^{ij})$ of the absorption-scattering coefficient in the medium, the measurement by the first measurement unit is modeled with a function f based on the light diffusion equation as in Equation 5, and an output $I_1$ is calculated:

$$f(r, \omega, S_0) \cdot P_{ij}(\mu_a^{ij}, \mu_s^{ij}) = I_1 \qquad \text{EQUATION 5}$$

An optimization is repeated by setting the distribution of the absorption-scattering characteristic until a difference between the signal $I_1$ calculated based on Equation 5 at each position of each light detector 13 and the actually measured value becomes equal to or smaller than a permissible error $\epsilon$. The first embodiment uses data obtained by the second measurement unit in addition to Equation 5. If a size L of the ultrasound focusing area, an irradiated ultrasonic intensity A, and an ultrasonic frequency $f_a$ are given, the modulation depth $m(\mu_a, \mu_s')$ can be calculated in the equation 4. When the measurement by the second measurement unit is modeled with a function g based on Equation 4 where $I_2$ is an output $I_2$, Equation 6 is expressed as follows:

$$g(r, r_k, A, f_a, L, S_0) \cdot P_{ij}(\mu_a^{ij}, \mu_s^{ij}) = I_2 \qquad \text{EQUATION 6}$$

Figure 2A:
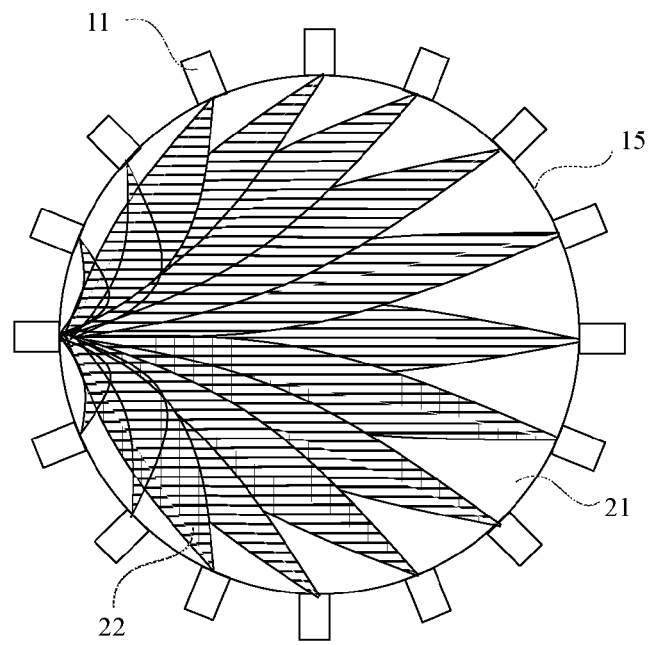
FIG. 2A is a schematic sectional view which shows a light propagation path in a measurement by a first measurement unit shown in FIG. 1A.
Figure 2B:
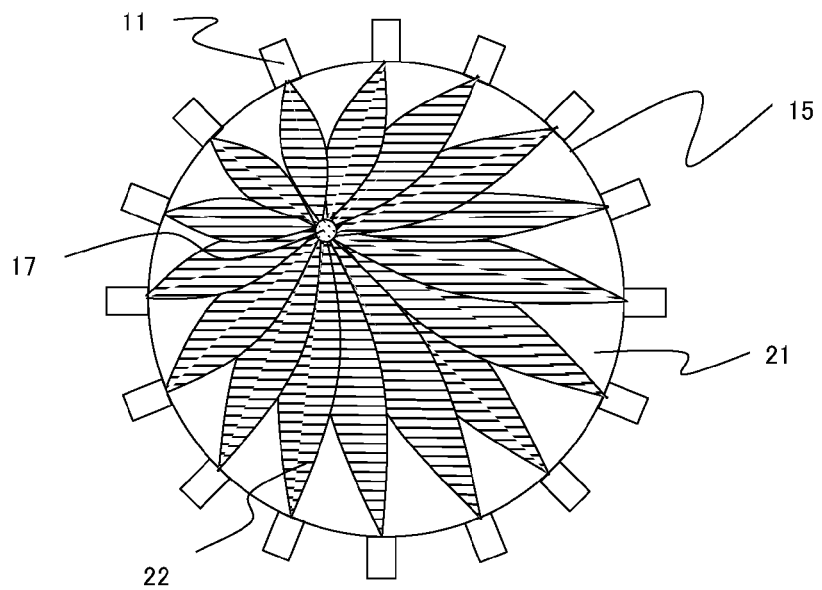
FIG. 2B is a schematic sectional view which shows a light propagation path in a measurement by a second measurement unit shown in FIG. 1A.

FIG. 2A shows a schematic light propagation path detected in the measurement by the first measurement unit, and FIG. 2B shows a schematic a light propagation path detected in the measurement by the second measurement unit. The light from the light source 3 is modulated at the measurement site X in the measurement by the second measurement unit, as if the modulation light source virtually stays inside the medium. Due to this virtual light source, the main propagation path of the light detected by each light detecting unit is different from the path of the light detected in the measurement by the first measurement unit shown in FIG. 2A.

The first measurement unit measures the diffused light that is diffused, propagates inside the measurement vessel 15, and follows a spatially spreading path. The second measurement unit measures the light that passes a local position of the measurement site X, and follows a spatially limited path. The measurement by the second measurement unit imposes a further limited condition than the measurement by the first measurement unit.

This embodiment assumes a distribution of the spectroscopic characteristic of the scattering medium, and changes the assumption such that a difference between a predicted value of the spectroscopic characteristic obtained in the assumption and the measured result obtained by the first measurement unit (a measured value obtained in the first step) can fall upon a permissible range. The (third) step of obtaining an optimal solution by changing the assumption uses the data obtained by the second measurement unit (the second step) for at least one of the parameter: the initial value, the constraint condition, and the boundary condition. A degree of freedom of solving an ill-posed problem can be limited by using the second measurement data based on Equation 6, rather than using only the first measurement data based on Equation 5. This approach can improve the precision of the image reconstruction.

Figure 3:
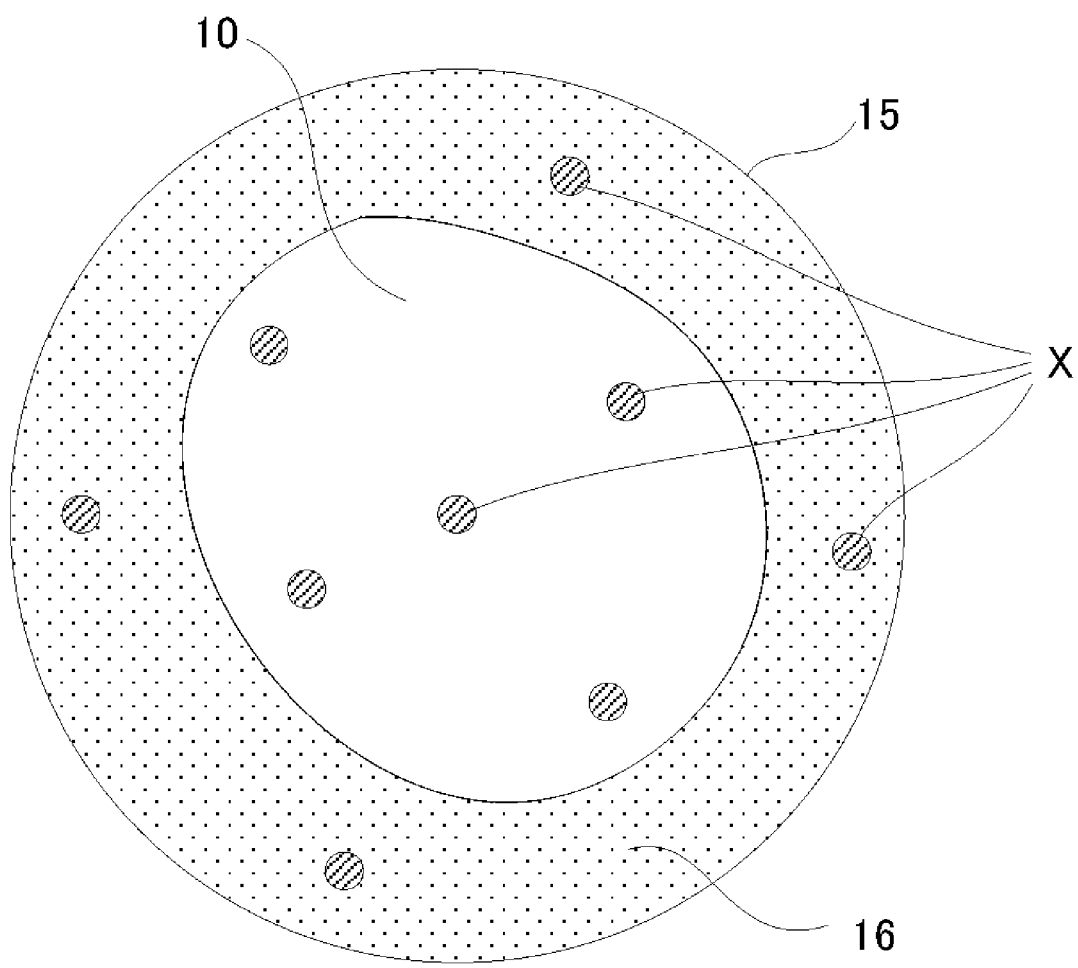
FIG. 3 is a schematic sectional view which shows ultrasound focusing positions in the second measurement unit shown in FIG. 1A.
Figure 4:
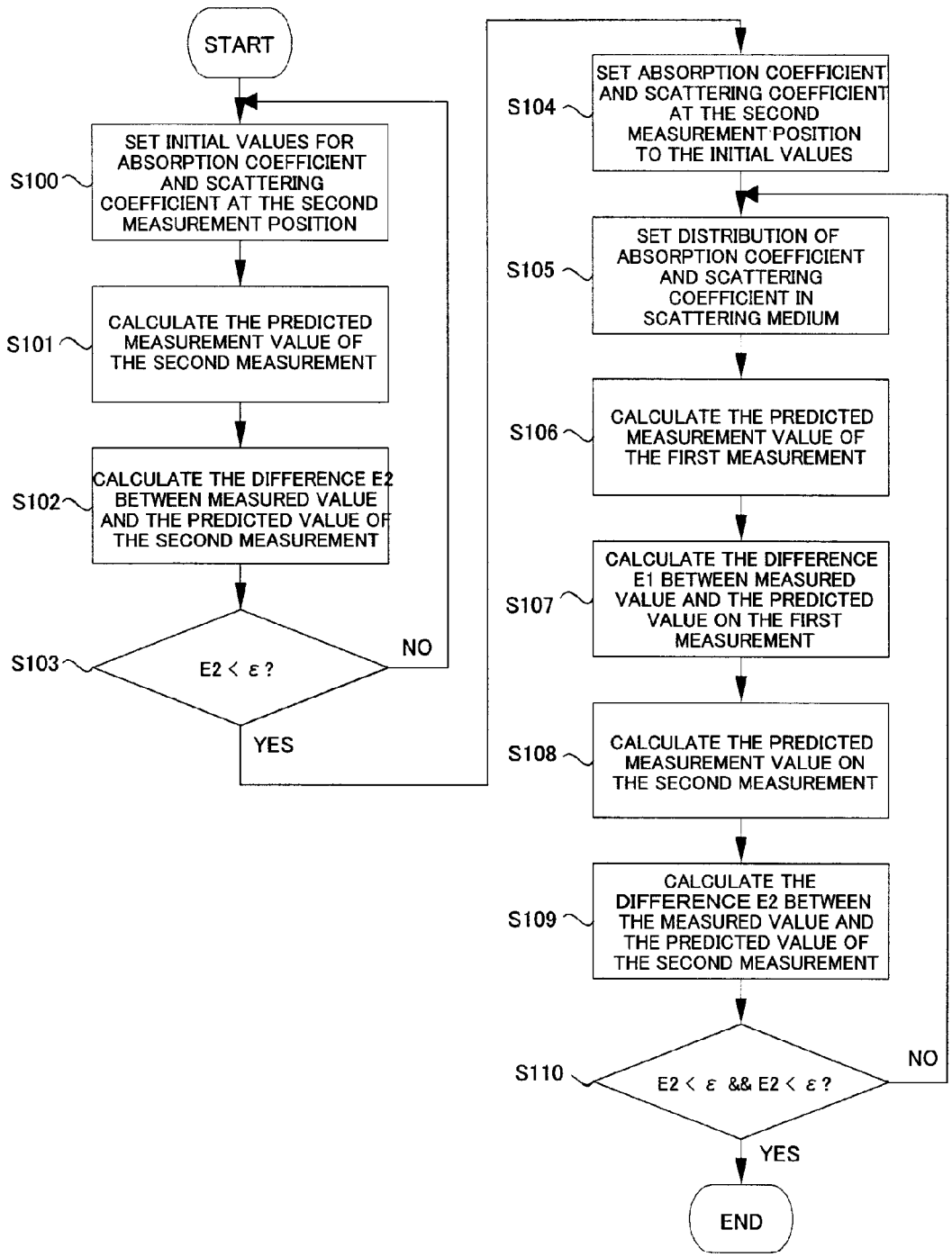
FIG. 4 is a flowchart for explaining an operation of a signal processing device in the measurement apparatus shown in FIG. 1A.

After the second measurement unit measures the measurement site X, the measurement site X is moved to an arbitrary and different position, and again measured by the second measurement unit. This flow is sequentially repeated, and as shown in FIG. 3, the second measurement unit measures plural measurement sites X so as to obtain the constraint condition given by Equation 6. FIG. 4 is a flowchart in the third step which is conducted by the signal processing unit 6.

First, based on the second measurement data, initial values for an absorption coefficient and a scattering coefficient are set to the ultrasound focusing position for each measurement, based on the second measurement data (S100). An initial value for a medium other than the ultrasound focusing position is also set. For example, values for an absorption coefficient and a scattering coefficient of the matching material 16 are set as an initial value. Each initial value is set for each mesh.

Once the absorption-scattering characteristic in the medium is set, the physical phenomenon is sequentially calculated as a forward problem in accordance with each measurement condition and the physical model described by the above equations in the measurement by the second measurement unit, and a predictable value of a detected signal is calculated (S101).

The signal calculated at S101 is compared with the actually measured signal, and a difference is calculated as an error E2 (S102). If E2 is greater than the permissible error $\epsilon$ that has been previously set, values for the absorption characteristic and the scattering characteristic of the measurement site X on the second measurement data are reset (S103). Then, the predicted measurement value is again calculated, the error E2 is obtained again, and the flow of the steps S100 to 103 is repeated until the error E2 becomes smaller than $\epsilon$. This flow is implemented for the entire second measurement data.

Once the error E2 becomes smaller than $\epsilon$, an inverse problem is estimated based on the first measurement data. Proper initial values for the absorption characteristic and scattering characteristic are obtained in the measurement site X by using the second measurement data in the flow up to S103. The obtained absorption coefficient and scattering coefficient are set as new initial values at the measurement site X (S104), and the initial values of the absorption coefficient and scattering coefficient of the medium other than the measurement site X are also reset (S105).

A predicted value is calculated based on the light diffusion equation in accordance the physical model in the measurement by the first measurement unit and the measurement condition (S106). An actually measured value that is obtained in the measurement by the first measurement unit is compared with the predicted value, an error E1 is calculated as a difference between these values (S107). Similarly, a predicted measured value is calculated by the second measurement unit in accordance with the physical model in the measurement by the second measurement unit and the measurement condition (S108), and an error E2 is calculated as a difference between these values (S109). Until both the errors E1 and E2 fall within the permissible error $\epsilon$ in S110, the distributions of the absorption coefficient and the scattering coefficient of the media in the measurement vessel are set for a calculation of a forward problem, and the flow of the steps S104 to S109 is repeated to compare the predicted value with the actually measured value. When the errors E1 and E2 become equal to or smaller than $\epsilon$, the image reconstruction by the signal processing unit 6 ends, and the distributions of the absorption coefficient and the scattering coefficient in the measurement vessel 15 are obtained. The permissible error $\epsilon$ may be set separately to the first measurement and the second measurement. The permissible error $\epsilon$ in S103 is not necessarily the same as the permissible error $\epsilon$ in S110 in the second measurement. This data is sent to the display unit 7, which outputs the data in turn. Spectroscopic information is obtained by similarly measuring and processing data for each of a plurality of the wavelengths. At this time, the signal processing unit 6 uses the Beer-Lambert law from the data on the absorption coefficient at each wavelength to calculate a ratio of a main ingredient of the scattering medium E, such as oxygenated hemoglobin, deoxygenated hemoglobin, water, lipid, and collagen, and functional information an oxygen saturation index from a hemoglobin concentration. The signal processing unit 6 also includes an image generating unit which constructs a three-dimensional tomographic view of spectroscopic information, a specific ingredient, and functional information of the scattering medium E. The display unit 7 displays a three-dimensional tomographic view.

A physical model used to calculate the light propagation in the image reconstruction may be a model based on a diffusion equation, a modeled light propagation by the Monte Carlo simulation, or the photon transportation equation.

This embodiment not only uses the second measurement data for a constraint condition but also shortens a calculation time period and obtains a precise image by setting local information to an initial value. Although the first measurement unit and the second measurement unit share the light detector 13 in this embodiment, they may use the different units.

Second Embodiment

A description will now be given of a measurement apparatus according to a second embodiment of the present invention. AOT and PAT can measure a spectroscopic characteristic better spatial resolution than DOT, but they have a smaller imaging depth than DOT. A configuration of the measurement apparatus of this embodiment is similar to that of the first embodiment, but the scattering medium E of this embodiment is larger than that of the first embodiment. A signal obtained by the second measurement unit is much smaller than a signal obtained by the first measurement unit since it is limited by the modulated light at the measurement site X. Accordingly, when the scattering medium E or the absorption characteristic is large, a measurable range of the second measurement unit in the scattering medium E is limited. When the light intensity that attenuates according to the light propagation distance lowers under a detectable limit of the light detector 13, the signal can no longer be detected. In this embodiment, the first measurement unit of this embodiment can measure an entire area in the scattering medium E, whereas the second measurement unit can measure only a part of the area in the scattering medium E.

Figure 5:
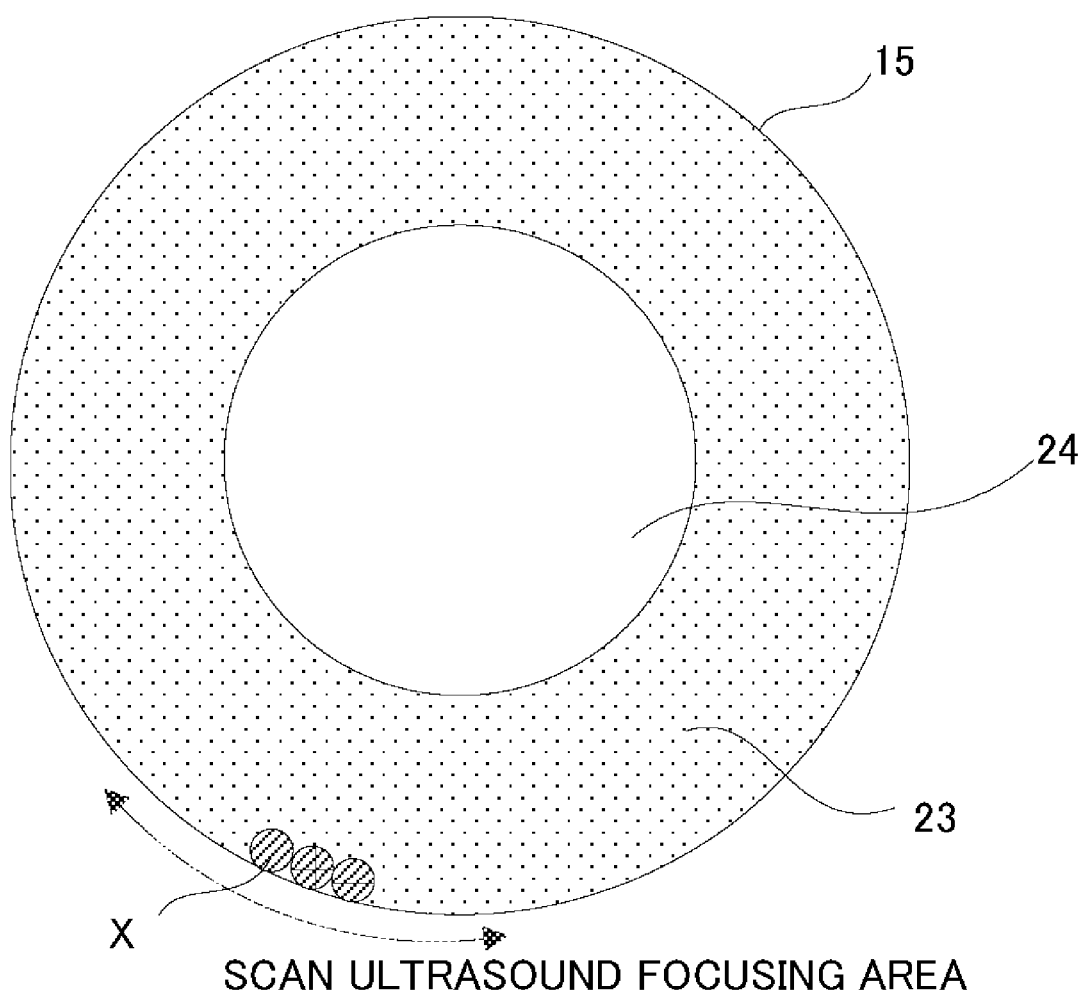
FIG. 5 is a schematic sectional view which shows a measurable range of a second measurement unit and an unmeasurable range of the second measurement unit.

A measurable area of the second measurement unit in the measurement vessel 15 is only a hatched doughnut shaped area 23 from the surface to a certain depth in the scattering medium E as shown in FIG. 5. The second measurement unit has difficulty in precisely measuring an area 24 inside the area 23, and only the first measurement unit can implement the precise measurement on the area 24.

The first measurement unit of this embodiment, similarly to the first embodiment, measures the entire spectroscopic characteristic in the measurement vessel 15. This embodiment uses, similarly to the first embodiment, the first measurement unit for the measurements, and stores the first measurement data with the measurement condition in the memory unit 5. For the area 23, the absorption-scattering distribution is obtained by scanning the measurement site X for each point in the measurement vessel 15 and measuring it with the second measurement unit. For the area 24, its absorption-scattering distribution is estimated by using the first measurement data and the absorption-scattering distribution obtained in the area 23 that is a measurable range of the second measurement unit.

Figure 6A:
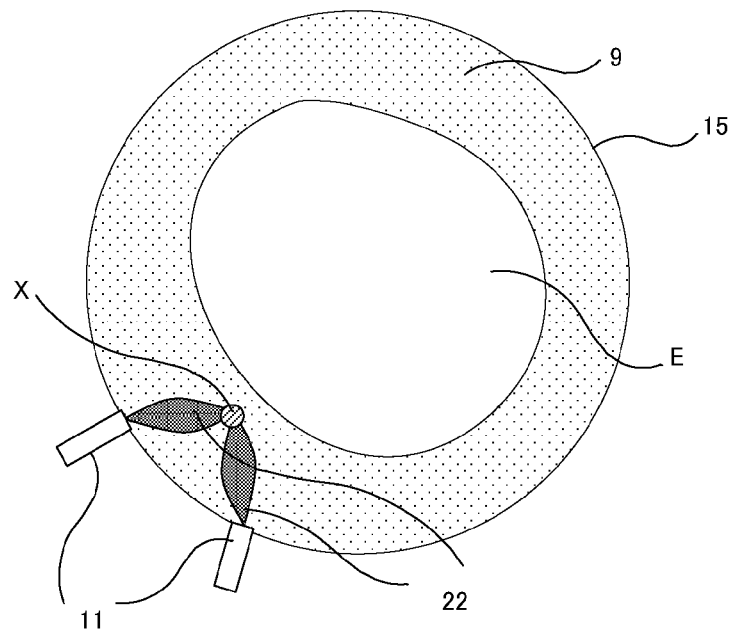
FIGS. 6A and 6B are schematic sectional views for explaining an operation of the second measurement unit according to the second embodiment.

When the measurement by the first measurement unit ends, the measurement site X is set in the area in the matching material 16, and is measured by the second measurement unit as shown in FIG. 6A. The absorption coefficient and the scattering coefficient of the matching material 16 are already known, and the detected light intensity in the medium having known absorption and scattering coefficients can be obtained once a light source fiber and detection fibers are selected as shown in FIG. 6A. These are treated as reference data.

Figure 6B:
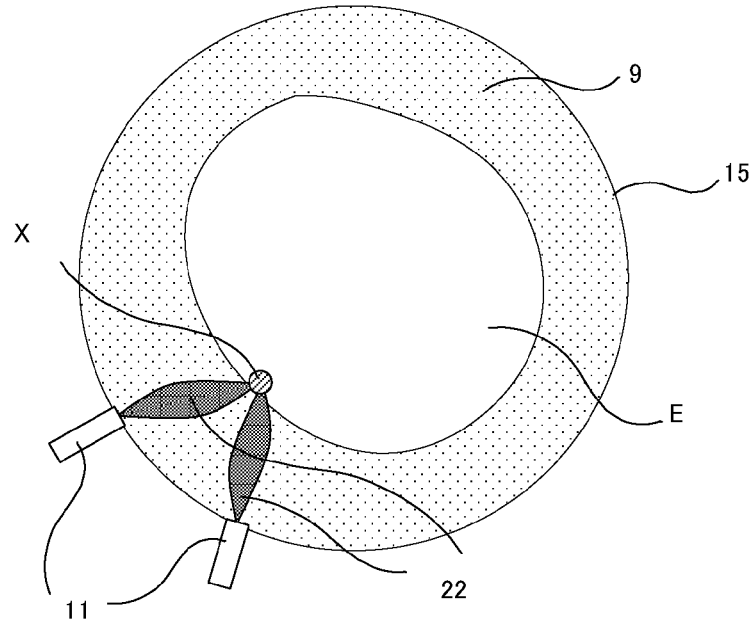

Next, as shown in FIG. 6B, the measurement site X is set in the scattering medium to implement the measurement. At this time, a measured value is compared with a calculated value in which the signal attenuation due to the light propagation distance is corrected so as to obtain differences from the reference data of the absorption and scattering coefficients. The data of the difference is used to obtain the local absorption and scattering coefficients at the measurement site X.

In this way, the absorption coefficient and the scattering coefficient are recursively obtained by using the measurement by the second measurement unit from the circumference of the measurement vessel 15. By gradually scanning the measurement site X from the area of the matching material 16 around the surface layer of the measured medium to the center of the measurement vessel 15, the second measurement unit measures the measurement site X until the second measurement unit can no longer measures the measurement site X. When a measurement becomes unavailable, the measurement ends.

Figure 7:
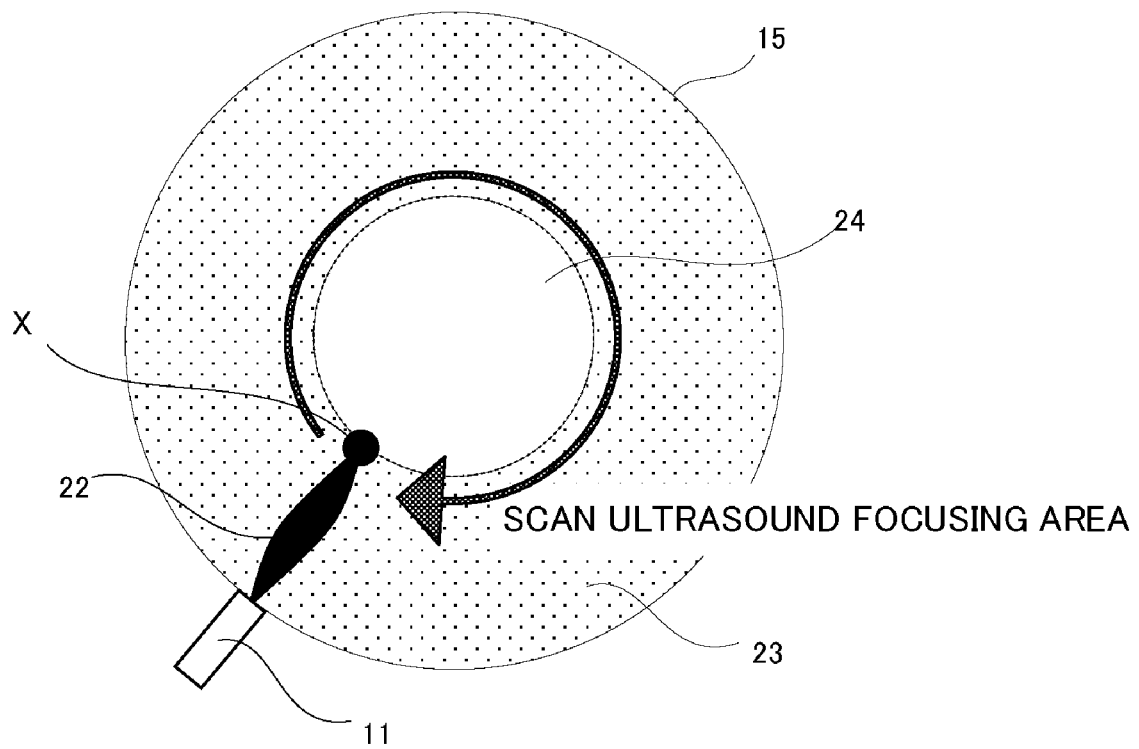
FIG. 7 is a schematic sectional view for explaining another operation of the second measurement unit.

Alternatively, the measurement site X is set and measured as shown in FIG. 7. For the area 23, the absorption coefficient and scattering coefficient are assumed for a certain calculation mesh. A result calculated in accordance with the model of Equation 6 using the above coefficients, is compared with the measurement result, and the absorption coefficient and the scattering coefficient of the area 23 are calculated.

As a result, the second measurement unit locally measures the absorption coefficient and the scattering coefficient of the area 23 shown in FIG. 5.

The signal processing unit 6 sequentially reads out the measurement condition and the measurement data from the memory unit 5, and implements an image reconstruction. Since the area 23 have known distributions of the absorption coefficient and the scattering coefficient with a size of each ultrasound focusing area, and they are given as solutions in the image reconstruction. Since the image of only the area 24 needs to be reconstructed, an estimation area becomes smaller than when the entire area of the measurement vessel needs an image reconstruction. In addition, an estimation time period is shortened because a solution for the area 23 has been already obtained by the second measurement unit, and this can be used as a boundary condition of the image reconstruction. The distributions of the absorption coefficient and the scattering coefficient of the area 24 are extrapolated from the area 23 having known absorption and scattering coefficients, and used as initial values for the image reconstruction.

An image reconstruction approach may use a model based on a diffusion equation, a modeled light propagation by the Monte Carlo simulation, or a photon transportation equation.

The tomographic view obtained in this embodiment has a fine resolution that is substantially the same as the ultrasound focusing size in the area 23. In the area 24, the spatial resolution and the measurement speed can be improved, for example, by reducing the ambient constraint condition or an estimation area. Thus, the spectroscopic characteristic of the scattering medium E can be comparatively easily or quickly obtained with a fine resolution.

This embodiment sets the measurement site X from the circumference of the measurement vessel 15, measures the measurement site X with the second measurement unit, and recursively calculates the absorption coefficient and the scattering coefficient. Alternatively, a signal relating to the absorption and the scattering may be calculated for each measurement site X in the entire area 23, and the absorption coefficient and the scattering coefficient which are obtained by the image reconstruction as a result of the measurements by the first measurement unit are used to calculate the absorption and scattering distributions for each measurement point of the measurement of by the second measurement unit.

Third Embodiment

Figure 8:
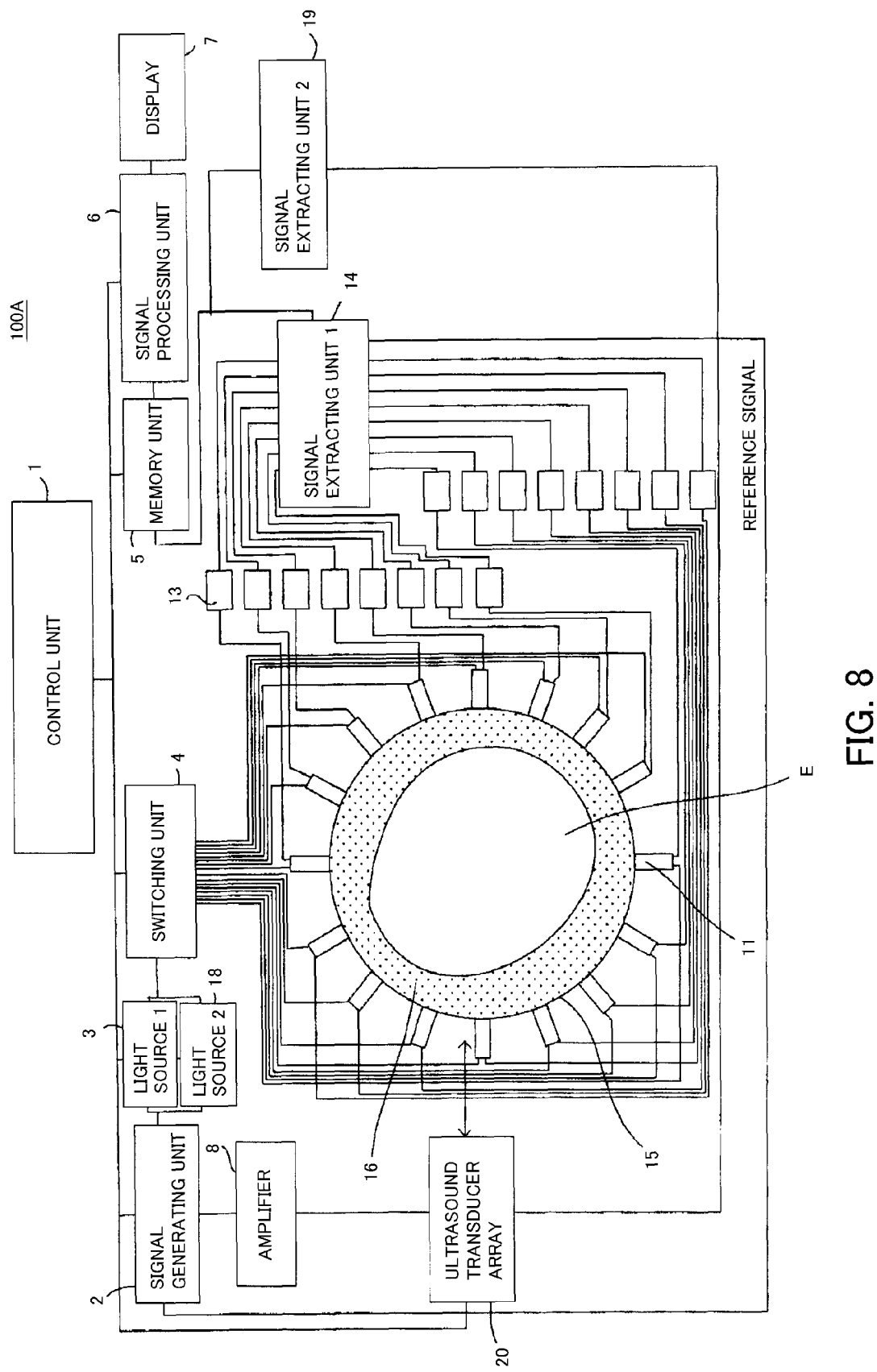
FIG. 8 is a block diagram of a measurement apparatus according to third and a forth embodiments of the present invention.

A description will now be given of the measurement apparatus according to the third embodiment of the present invention. FIG. 8 is a block diagram of a measurement apparatus 100A according to the third embodiment. The measurement apparatus 100A further includes a light source 18, a signal extraction unit 19, and an ultrasonic transducer array 20. The measurement of the first measurement unit is similar to the measurement apparatus 100, and a description will now be given of the second measurement unit. The second measurement unit of this embodiment measures a spectroscopic characteristic of the measurement site X by using PAT.

The light 18 guides the pulsed light having several tens of nano-seconds to the fibers 11, and the switching unit 4 selects some fibers 11 for light sources so as to irradiate the pulsed light into the measurement vessel 15. Each fiber 11 selected as the light source belongs to a group of fibers that is arranged adjacent to the measurement vessel 15. The light that enters the measurement vessel 15 is diffused in the measurement vessel. When the light is absorbed in the scattering medium E, the energy loss by the absorption is converted into the heat. When a stress confining condition is met such that the pulse width of the light can become shorter than a stress relaxation time period, an elastic wave is emitted through the heat elastic process. A pressure P (r) of the elastic wave where r is a position in the scattering medium is generally given by the following equation:

$$P(r) = \frac{1}{2}\Gamma\mu_a(r)\Phi(r) \qquad \text{EQUATION 7}$$

$\Gamma$ is a Gruneisen coefficient (heat-acoustic conversion efficiency). $\mu_a(r)$ is an absorption coefficient at the position r. $\Phi(r)$ is a fluence rate of a photon at the position r.

As indicated in Equation 7, the elastic wave is a pressure wave proportional to a local absorption coefficient of the light, and the absorption coefficient can be estimated from an acoustic signal. A local absorption coefficient can be measured since the generated elastic wave is free of the influence of scattering unlike the light. The transmittable and receivable transducer array 20 detects the elastic wave from the measurement site X, and the signal extracting unit 19 obtains the absorption coefficient based on a sound pressure distribution of the signal. The measurement site X is arbitrarily set, and the absorption coefficient is estimated by detecting the elastic wave. The fibers used as the light sources can be close to the measurement site X set by the ultrasound transducer array 20.

The second measurement unit measures a plurality of arbitrary points in the measurement vessel 15, and the measured absorption coefficients are stored in the memory unit 5. In estimating the absorption coefficient from the detected elastic wave, the sound pressure on the matching material 16 may be previously measured and used for the calibration. When the measurement by the first measurement unit and the measurement by the second measurement unit end, the signal processing unit 6 provides an image reconstruction. A plurality of the local absorption coefficients obtained by the second measurement unit are spatially interpolated in order to obtain a distribution of the absorption coefficient, and the distribution is set as an initial value for the image reconstruction. A relative distribution of the absorption coefficient is set as an initial value, and the signal processing unit 6 estimates distributions of the absorption and scattering coefficients in the scattering medium through the image reconstruction.

Fourth Embodiment

A descriptions will now be given of the measurement apparatus according to the forth embodiment of the present invention. A configuration of the measurement apparatus of this embodiment is similar to that of the third embodiment. The first measurement data is obtained similarly to the third embodiment, and stored in the memory unit 5. This embodiment characteristically operates the ultrasound transducer array 20 as an ultrasound echo device.

Next, the signal generating device 2 drives the ultrasound transducer array 20 through the amplifier 8. An ultrasound focusing device not shown in the figure, which focuses ultrasound on a certain position in the measurement vessel 15, is connected to the ultrasound transducer array 20. The ultrasound transducer array 20 captures an echo signal which is reflected according to the acoustic impedance at the ultrasound focusing position. A structural characteristic can be measured (forth step) by scanning the focusing position of the transducer array 20, and the data is stored in the memory unit 5.

Next, the signal processing unit 6 reads out the structure information on the scattering medium E obtained by detecting the ultrasonic echo, and extracts an apparently structurally characteristic portion. For example, an ultrasonic echo image is edge-treated, a structural boundary is extracted, a positional coordinate is obtained, and the structure information is stored in the memory unit 5. The second measurement unit implements the measurement by using the structure information. First, the apparently structurally characteristic portion which has been obtained by the edge extraction is read out from the memory unit 5, and the vicinity is set as the focusing position of the ultrasonic transducer array 20. The fibers that are relatively close to the position are used as light sources, the pulsed light is introduced from the measurement site X into the measurement vessel 15, and the elastic wave generated from the above focusing position is measured by the ultrasound transducer array 20.

The signal extracting unit 19 obtains the absorption coefficient at the measurement site X based on the sound pressure distribution of the signal detected by the ultrasound transducer array 20. The second measurement unit measures the vicinity of the structurally characteristic portion obtained by the edge extraction. The focusing position of the ultrasound transducer array 12 is set near the structural edge read out from the memory unit 5, and the second measurement data is obtained. This is stored in the memory unit 5.

An apparently structurally changing portion is highly likely to have a different organic and optical characteristic. When the second measurement unit intensively measures a spectroscopic characteristic in this area, the absorption and scattering distributions can be precisely obtained in reconstructing an image from the first measurement data.

The thus obtained distribution of the absorption coefficient is set as an initial value, and the image is reconstructed by using the first measurement data. The above embodiments may be combined with each other. For example, the ultrasound echo may be combined with AOT. In addition, the second measurement data may be used for one or more of the initial value, the constraint condition, or the boundary condition in the image reconstruction.

As described above, the first to fourth embodiments can increase conditions in estimating an inverse problem in DOT by using AOT or PAT measurement, thereby avoiding an ill-posed problem, improving an estimation precision or a spatial resolution of the absorption-scattering characteristic of the scattering medium E, and shortening an estimation time period. Further, these embodiments can maintain the reproducibility irrespective of an arrangement of the light source and the light detector.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims a foreign priority benefit based on Japanese Patent Application No. 2007-237010, filed on Sep. 9, 2007, which is hereby incorporated by reference herein in its entirety as if fully set forth herein.

What is claimed is:

1. A measurement method of measuring a spectroscopic characteristic inside of a scattering medium, said measurement method comprising:
   a first step of measuring the spectroscopic characteristic of the scattering medium by using diffuse optical tomography by irradiating light into the scattering medium;
   a second step of measuring the spectroscopic characteristic of the scattering medium by using acousto-optical tomography or photo acoustic tomography by irradiating light into the scattering medium; and
   a third step of making an assumption of a distribution of the spectroscopic characteristic inside of the scattering medium and of changing the assumption such that a difference between a predicted value of the spectroscopic characteristic derived from the assumption and a measured value obtained in the first step can fall upon a permissible range,
   wherein the third step uses data obtained in the second step for at least one of the parameter: an initial value, a constraint condition, or a boundary condition.

2. A measurement method according to claim 1, wherein the third step estimates the distribution of the spectroscopic characteristic of the scattering medium by using data in a measurable range of the second step, and estimates the distribution of the spectroscopic characteristic of the scattering medium by using data obtained in the first step and the data obtained in the second step in an unmeasurable range of the second step.

3. A measurement method according to claim 1, wherein the third step estimates the distribution of the spectroscopic characteristic of the scattering medium by further using data obtained by spatially interpolating the data.

4. A measurement method according to claim 1, further comprising a forth step of measuring a structural characteristic of the scattering medium using an ultrasonic echo,
wherein the first step estimates the distribution of the spectroscopic characteristic of the scattering medium by further using data of a portion that indicates a variation in the structural characteristic obtained in the forth step.

5. A measurement method according to claim 1, further comprising:
a step of generating a three-dimensional tomographic image of the scattering medium by using the spectroscopic characteristic or by calculating a concentration and a constituent ratio of an ingredient that contributes to an absorption in the spectroscopic characteristic; and
a step of displaying the three dimensional tomographic image.

6. A measurement apparatus configured to measure a spectroscopic characteristic inside of a scattering medium, said measurement apparatus comprising:
a first measurement unit configured to measure the spectroscopic characteristic of the scattering medium by using diffuse optical tomography;
a second measurement unit configured to measure the spectroscopic characteristic of the scattering medium by using acousto-optical tomography or photo acoustic tomography; and
a signal processing unit configured to make an assumption of a distribution of the spectroscopic characteristic inside of the scattering medium and to change the assumption such that a difference between a predicted value of the spectroscopic characteristic derived from the assumption and a measured value obtained in the first measurement unit can fall upon a permissible range,
wherein the signal processing unit uses data obtained in the second measurement unit for at least one of the parameter: an initial value, a constraint condition, or a boundary condition.

* * * * *